(12) United States Patent
Viswanath et al.

(10) Patent No.: US 10,890,674 B2
(45) Date of Patent: Jan. 12, 2021

(54) DYNAMIC NOISE SHAPING IN A PHOTON COUNTING SYSTEM

(71) Applicant: Texas Instruments Incorporated, Dallas, TX (US)

(72) Inventors: Rakul Viswanath, Bangalore (IN); Nagesh Surendranath, Bangalore (IN); Sandeep Kesrimal Oswal, Bangalore (IN); Ratna Kumar Venkata Parupudi, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 78 days.

(21) Appl. No.: 16/247,639

(22) Filed: Jan. 15, 2019

(65) Prior Publication Data
US 2020/0225370 A1 Jul. 16, 2020

(51) Int. Cl.
*G01T 1/24* (2006.01)
*A61B 6/03* (2006.01)
*A61B 6/00* (2006.01)
*H03F 3/70* (2006.01)
*H03M 1/46* (2006.01)

(52) U.S. Cl.
CPC .............. *G01T 1/247* (2013.01); *A61B 6/032* (2013.01); *A61B 6/4241* (2013.01); *H03F 3/70* (2013.01); *H03M 1/46* (2013.01)

(58) Field of Classification Search
CPC ....... G01T 1/247; A61B 6/032; A61B 6/4241; H03F 3/70; H03M 1/46
See application file for complete search history.

(56) References Cited

U.S. PATENT DOCUMENTS

| | | |
|---|---|---|
| 4,070,578 A | 1/1978 | Timothy et al. |
| 4,255,659 A | 3/1981 | Kaufman et al. |
| 4,595,909 A | 6/1986 | Jarrett |
| 4,647,903 A | 3/1987 | Ryu |
| 5,508,507 A | 4/1996 | Nelson et al. |
| 5,693,946 A | 12/1997 | Vickers et al. |
| 5,943,388 A | 8/1999 | Tumer |
| 6,300,635 B1 | 10/2001 | Brambilla et al. |
| 6,324,244 B1 | 11/2001 | Lauter et al. |
| 6,678,039 B2 | 1/2004 | Charbon |
| 6,781,134 B1 | 8/2004 | Murray |
| 6,917,041 B2 | 7/2005 | Doty et al. |
| 6,998,913 B2 | 2/2006 | DeGeronimo |
| 7,065,175 B2 | 6/2006 | Green |
| 7,139,024 B2 | 11/2006 | Lu et al. |
| 7,157,715 B1 | 1/2007 | Crain, Jr. et al. |
| 7,157,716 B2 | 1/2007 | Kitaguchi et al. |
| 7,170,049 B2 | 1/2007 | Iwanczyk et al. |
| 7,233,979 B2 | 6/2007 | Dickerman et al. |
| 7,250,896 B1 | 7/2007 | Hesener |
| 7,339,175 B1 | 3/2008 | Drummond et al. |

(Continued)

*Primary Examiner* — Courtney D Thomas
(74) *Attorney, Agent, or Firm* — John R. Pessetto; Charles A. Brill; Frank D. Cimino

(57) ABSTRACT

In described examples, a charge sensitive amplifier (CSA) generates an integrated signal in response to a current signal. A high pass filter is coupled to the CSA and receives the integrated signal and an inverse of an event signal, the high pass filter generates a coarse signal. An active comparator is coupled to the high pass filter and receives the coarse signal and a primary reference voltage signal, the active comparator generates the event signal.

21 Claims, 5 Drawing Sheets

(56) References Cited

U.S. PATENT DOCUMENTS

| | | |
|---|---|---|
| 7,362,175 B2 | 4/2008 | Arques |
| 7,368,722 B2 | 5/2008 | Berthold et al. |
| 7,388,210 B2 | 6/2008 | Ouvrier-Buffet et al. |
| 7,501,965 B2 | 3/2009 | Janakiraman |
| 7,514,688 B2 | 4/2009 | Boroennimann et al. |
| 7,528,375 B2 | 5/2009 | Matsumoto |
| 7,582,878 B2 | 9/2009 | Shahar et al. |
| 7,592,603 B2 | 9/2009 | Hsi et al. |
| 7,615,753 B2 | 11/2009 | Audebert et al. |
| 7,615,755 B2 | 11/2009 | Coello et al. |
| 7,634,061 B1 | 12/2009 | Tumer et al. |
| 7,738,631 B2 | 6/2010 | Rundle |
| 7,760,123 B2 | 7/2010 | Rao et al. |
| 7,818,047 B2 | 10/2010 | Tumer et al. |
| 7,868,665 B2 | 1/2011 | Tumer et al. |
| 8,044,681 B2 | 10/2011 | Rao et al. |
| 8,159,286 B2 | 4/2012 | Rao et al. |
| 8,170,175 B2 | 5/2012 | Kasuya |
| 8,198,577 B2 | 6/2012 | Dierickx |
| 8,213,566 B2 | 7/2012 | Roessl et al. |
| 8,258,480 B2 | 9/2012 | Olcott et al. |
| 8,260,565 B2 | 9/2012 | DeGeronimo |
| 8,269,180 B2 | 9/2012 | DeGeronimo |
| 8,299,670 B2 | 10/2012 | Krumme |
| 8,338,773 B2 | 12/2012 | Eldesouki et al. |
| 8,373,135 B2 | 2/2013 | Kappler |
| 8,378,310 B2 | 2/2013 | Bornefalk et al. |
| 8,384,038 B2 | 2/2013 | Guo et al. |
| 8,415,635 B2 | 4/2013 | Marks et al. |
| 8,426,828 B2 | 4/2013 | Dierickx |
| 8,440,957 B2 | 5/2013 | Dierickx |
| 8,491,190 B2 | 7/2013 | Glasser et al. |
| 8,493,260 B2 | 7/2013 | Chu et al. |
| 8,530,850 B2 | 9/2013 | Spartiotis et al. |
| 8,610,081 B2 | 12/2013 | Rao et al. |
| 8,618,495 B2 | 12/2013 | DeGeronimo |
| 8,618,975 B2 | 12/2013 | Nys et al. |
| 8,680,474 B2 | 3/2014 | Soh et al. |
| 8,692,176 B2 | 4/2014 | Kelly et al. |
| 8,716,643 B2 | 5/2014 | Eldesouki et al. |
| 8,729,485 B2 | 5/2014 | Soh et al. |
| 8,748,832 B2 | 6/2014 | Brambilla et al. |
| 8,766,198 B2 | 7/2014 | Dinapoli et al. |
| 8,772,730 B2 | 7/2014 | Han et al. |
| 8,816,290 B2 | 8/2014 | Hamlin |
| 8,816,292 B2 | 8/2014 | Cui et al. |
| 8,859,944 B2 | 10/2014 | Eldesouki et al. |
| 8,866,094 B2 | 10/2014 | Tsukiyama et al. |
| 8,866,097 B2 | 10/2014 | Meng |
| 8,866,662 B1 | 10/2014 | Naumov |
| 8,891,845 B2 | 11/2014 | Ogawa et al. |
| 8,981,985 B2 | 3/2015 | Lian et al. |
| 8,988,267 B1 | 3/2015 | Kimura et al. |
| 9,014,455 B2 | 4/2015 | Oh et al. |
| 9,029,793 B2 | 5/2015 | Spartiotis et al. |
| 9,081,103 B2 | 7/2015 | Loeliger et al. |
| 9,086,494 B2 | 7/2015 | Han et al. |
| 9,116,249 B1 | 8/2015 | Claus et al. |
| 9,121,955 B2 | 9/2015 | Schmitt et al. |
| 9,128,195 B2 | 9/2015 | Soh et al. |
| 9,185,314 B2 | 11/2015 | Mantri et al. |
| 9,213,108 B2 | 12/2015 | Nagai |
| 9,239,391 B2 | 1/2016 | Han et al. |
| 9,254,113 B2 | 2/2016 | Kim et al. |
| 9,274,235 B2 | 3/2016 | Kang et al. |
| 9,297,912 B2 | 3/2016 | Campbell et al. |
| 9,310,495 B2 | 4/2016 | Spartiotis et al. |
| 9,301,378 B2 | 5/2016 | Steadman Booker et al. |
| 9,351,701 B2 | 5/2016 | Yamakawa et al. |
| 9,354,331 B2 | 5/2016 | Sagoh et al. |
| 9,417,339 B2 | 8/2016 | Spahn |
| 9,437,771 B2 | 9/2016 | Deptuch |
| 9,444,344 B2 | 9/2016 | Kim et al. |
| 9,461,664 B2 | 10/2016 | Sampath |
| 9,517,045 B2 | 12/2016 | Kang et al. |
| 9,538,107 B2 | 1/2017 | Chappo |
| 9,588,238 B2 | 3/2017 | Kim et al. |
| 9,588,239 B2 | 3/2017 | Abraham et al. |
| 9,595,101 B2 | 3/2017 | Kato et al. |
| 9,599,730 B2 | 3/2017 | Spahn |
| 9,602,747 B2 | 3/2017 | Scott et al. |
| 9,608,652 B2 | 3/2017 | Lee et al. |
| 9,664,797 B2 | 5/2017 | Roessl et al. |
| 9,664,798 B2 | 5/2017 | Kappler et al. |
| 9,678,220 B2 | 6/2017 | Herrmann |
| 9,696,432 B2 | 7/2017 | Ouvrier-Buffet |
| 9,700,268 B2 | 7/2017 | Kang et al. |
| 9,702,758 B2 | 7/2017 | Nouri |
| 9,730,665 B2 | 8/2017 | Choi et al. |
| 9,736,398 B2 | 8/2017 | Kim et al. |
| 9,750,471 B2 | 9/2017 | Schirra et al. |
| 9,753,160 B2 | 9/2017 | Bellazzini |
| 9,759,822 B2 | 9/2017 | Daerr et al. |
| 9,806,552 B2 | 10/2017 | Brannick et al. |
| 9,952,333 B2 | 4/2018 | Abraham et al. |
| 9,958,557 B2 | 5/2018 | Kim et al. |
| 10,151,845 B1 | 12/2018 | Viswanath et al. |
| 2008/0149842 A1* | 6/2008 | El-Hanany ............ G01T 1/2928 250/370.09 |
| 2009/0046181 A1 | 2/2009 | Olsen et al. |
| 2014/0232582 A1 | 8/2014 | Lian et al. |
| 2017/0119325 A1 | 5/2017 | Tamura |
| 2017/0160129 A1 | 6/2017 | Viswanath et al. |
| 2018/0049707 A1 | 2/2018 | Ishitsu et al. |
| 2018/0292551 A1* | 10/2018 | Danielsson ............ G01T 1/2985 |

\* cited by examiner

DYNAMIC NOISE SHAPING IN A PHOTON COUNTING SYSTEM

TECHNICAL FIELD

This relates generally to medical diagnostic devices, and more particularly to a photon counting system in imaging systems.

BACKGROUND

Computed tomography (CT) is a medical imaging technique that produces three-dimensional images of internal human body parts from a large series of two-dimensional X-ray images (called profiles) taken in a single-axis rotating structure called a gantry. When compared to a conventional X-ray radiograph, which is an image of many planes superimposed on each other, a CT image has significantly improved contrast.

For diagnostic imaging systems like CT, which require complex and intensive image processing, semiconductors play a very important role in developing systems with increased density, flexibility and high performance. The helical or spiral CT machines have faster computer systems and optimized software to continuously process the cross-section images while a patient/object passes through the gantry at a constant speed.

An X-ray source rotates around the object, and X-ray detectors (positioned on an opposite side of the patient/object from the X-ray source) generate X-ray slice data. Many data scans are taken progressively as the patient/object gradually passes through the gantry. A data acquisition system includes multiple X-ray detectors, and each X-ray detector includes multiple channels.

Accordingly, X-ray detectors receive the X-rays attenuated by the patient/object and generate proportional current signals. The current signals are further converted into digital signals. The conventional CT systems also utilize spectral information embedded in the received X-rays. The spectral information represents a variation in the energy (or energy resolution) of photons received by the detector. Some X-ray detectors include a photon counting system to derive the spectral information. The conventional photon counting systems include a high bandwidth amplifier to obtain the spectral information. However, conventional systems consume a large amount of power to drive the amplifier and to meet a particular noise specification.

SUMMARY

In described examples, a circuit includes a charge sensitive amplifier (CSA) that generates an integrated signal in response to a current signal. A high pass filter is coupled to the CSA and receives the integrated signal and an inverse of an event signal, the high pass filter generates a coarse signal. An active comparator is coupled to the high pass filter and receives the coarse signal and a primary reference voltage signal, the active comparator generates the event signal.

DETAILED DESCRIPTION OF EXAMPLE EMBODIMENTS

Figure 1:
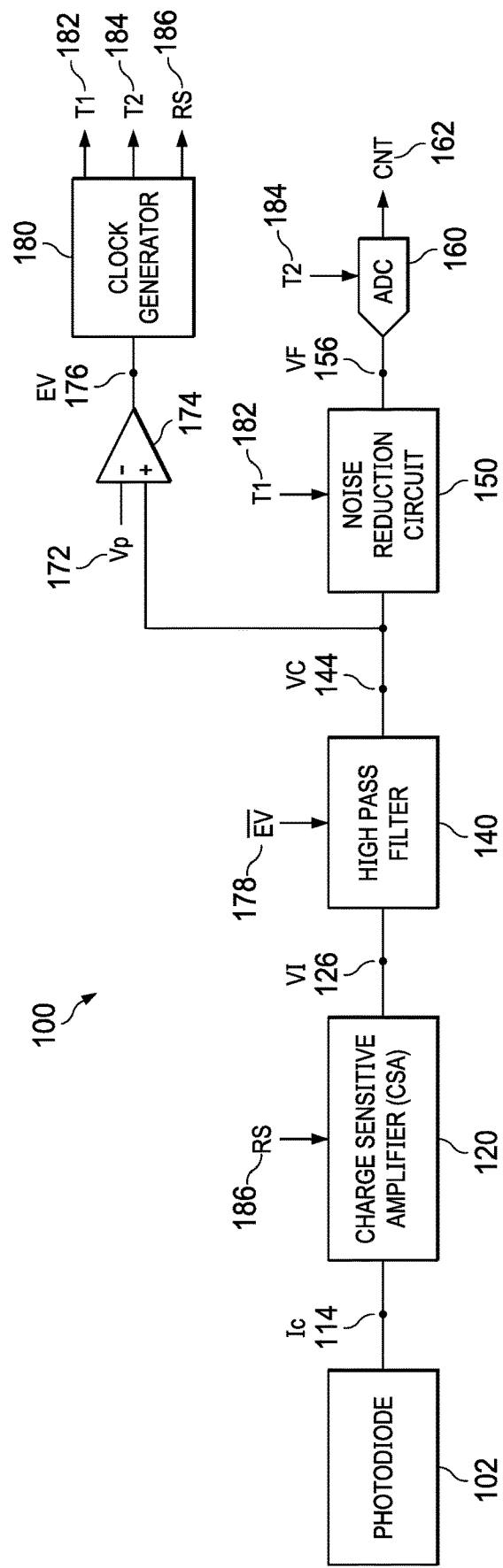
FIG. 1 is a block diagram of a circuit, according to an embodiment.

FIG. 1 is a block diagram of a circuit 100, according to an embodiment. The circuit 100 includes a photodiode 102 and a charge sensitive amplifier (CSA) 120. The CSA 120 is coupled to the photodiode 102. The circuit 100 also includes a high pass filter 140 and a noise reduction circuit 150. The high pass filter 140 is coupled to the CSA 120. The noise reduction circuit 150 is coupled to the high pass filter 140. The circuit 100 includes an analog to digital converter (ADC) 160 coupled to the noise reduction circuit 150.

The circuit 100 also includes an active comparator 174 and a clock generator 180. The active comparator 174 is coupled to the high pass filter 140. The clock generator 180 is coupled to the active comparator 174. The circuit 100 may include one or more additional components that are not described herein for simplicity of the description.

In operation of the circuit 100 (FIG. 1), the photodiode 102 receives light which includes multiple photons of different energies. The photodiode 102 generates a proportional current signal Ic 114 when these photons are incident on the photodiode 102. In another example, the photodiode 102 receives an energy signal and generates the proportional current signal Ic 114. The CSA 120 receives the current signal Ic 114 generated by the photodiode 102. The CSA 120 generates an integrated signal VI 126 in response to the current signal Ic 114. In one version, the CSA 120 integrates the current signal Ic 114 to generate the integrated signal VI 126. A reset signal RS 186 resets the CSA 120.

The high pass filter 140 receives the integrated signal VI 126 and an inverse of an event signal $\overline{EV}$ 178. The high pass filter 140 generates a coarse signal VC 144 in response to the integrated signal VI 126 and the inverse of the event signal $\overline{EV}$ 178. In one version, the high pass filter 140 filters the integrated signal VI 126 to generate the coarse signal VC 144. The active comparator 174 receives the coarse signal VC 144 and a primary reference voltage signal Vp 172. The active comparator 174 compares the coarse signal VC 144 and the primary reference voltage signal Vp 172 and generates an event signal EV 176. The event gate EV 176 is provided to a NOT gate which generates the inverse of the event signal $\overline{EV}$ 178. Thus, the event signal EV 176 and the inverse of the event signal $\overline{EV}$ 178 are complement of each other.

The clock generator 180 generates a first trigger signal T1 182, a second trigger signal T2 184 and the reset signal RS 186 in response to the event signal EV 176 received from the active comparator 174. The clock generator 180 adds a first delay to the event signal EV 176 to generate the first trigger signal T1 182. The clock generator 180 adds a second delay to the event signal EV 176 to generate the second trigger signal T2 184. The clock generator 180 adds a third delay to the event signal EV 176 to generate the reset signal RS 186.

When the event signal EV 176 is at logic high, the clock generator 180 generates the first trigger signal T1 182 after the first delay, the second trigger signal T2 184 after the second delay and the reset signal RS 186 after the third delay. In one example, the third delay is greater than the second delay, and the second delay is greater than the first delay. In another example, the third delay is equal to the second delay. The noise reduction circuit 150 receives the coarse signal VC 144 and the first trigger signal T1 182, and generates a fine signal VF 156. The ADC 160 generates a count signal CNT 162 in response to the fine signal VF 156 and the second trigger signal T2 184.

The high pass filter 140 is operational while the event signal EV 176 is at logic low. Thus, the high pass filter 140 filters any low frequency noise in the integrated signal VI 126, and thus prevents the low frequency noise from reaching the ADC 160 when no light or a signal less than the primary reference voltage signal Vp 172 is received by the photodiode 102 or when the system including circuit 100 is idle. The high pass filter 140 prevents any signal whose frequency is less than a cut-off frequency of the high pass filter 140 from reaching the ADC 160 and the active comparator 174.

An 'event' occurs when an X-ray photon is incident on the photodiode 102, and a proportional current signal Ic 114 is generated. The CSA 120 generates the integrated signal VI 126 in response to the current signal Ic 114. The high pass filter 140 generates the coarse signal VC 144 in response to the integrated signal VI 126 and the inverse of the event signal $\overline{EV}$ 178. The active comparator 174 is always active. In one example, the active comparator 174 does not generate the event signal EV 176 when the coarse signal VC 144 is less than the primary reference voltage signal Vp 172. The active comparator 174 toggles or generates the event signal EV 176 when the coarse signal VC 144 is greater than the primary reference voltage signal Vp 172.

When the event signal EV 176 is generated i.e. the event signal EV 176 is at logic high, the high pass filter 140 is disabled. The clock generator 180 generates the first trigger signal T1 182, the second trigger signal T2 184 and the reset signal RS 186 in response to the event signal EV 176 received from the active comparator 174. The first trigger signal T1 182, the second trigger signal T2 184 and the reset signal RS 186 are generated only when the event signal EV 176 is at logic high.

The clock generator 180 adds a first delay to the event signal EV 176 to generate the first trigger signal T1 182. In one example, the first delay is equivalent to a time consumed by the circuit 100 to acquire most of the charge when the light that includes multiple photons is received by the photodiode 102. The exact value of the first delay is optimized for minimum noise in the fine signal VF 156 at the end of the second delay based on a transient response of the photodiode 102 and the CSA 120. In another example, the first delay is equal to a predefined time after the event signal EV 176 is generated. In yet another example, the first delay is in a range of 4-10 nano seconds after the event signal EV 176 is generated.

On receiving the first trigger signal T1 182 from the clock generator 180, the noise reduction circuit 150 blocks any high frequency noise of the CSA 120 sampled by the high pass filter 140. Once enabled, the noise reduction circuit 150 prevents any high frequency noise from the CSA 120 or the high pass filter 140 to be passed to the ADC 160. As a result, no additional power is required to reduce noise in the circuit 100. The noise reduction circuit 150 blocks the high frequency noise only for a time period when it receives the first trigger signal T1 182.

The first trigger signal T1 182 is inactivated before generation of the second trigger signal T2 184. The clock generator 180 adds the second delay to the event signal EV 176 to generate the second trigger signal T2 184. On receiving the second trigger signal T2 184, the ADC 160 samples the fine signal VF 156 to generate the count signal CNT 162. A time interval during which the second trigger signal T2 184 is activated or is at logic high depends on a sampling frequency of the ADC 160.

The clock generator 180 adds a third delay to the event signal EV 176 to generate the reset signal RS 186. In one example, the reset signal RS 186 is generated by the clock generator 180 when the second trigger signal T2 184 is inactivated. The reset signal RS 186 causes resetting of the CSA 120.

The resetting of the CSA 120 causes the event signal EV 176 to go to logic low. This enables the high pass filter 140. The high pass filter 140 filters any low frequency noise in the integrated signal VI 126, and thus prevents the low frequency noise from reaching the ADC 160 when no light is received by the photodiode 102 or when the system including circuit 100 is idle. The high pass filter 140 prevents any signal whose frequency is less than a cut-off frequency of the high pass filter 140 from reaching the ADC 160 and the active comparator 174. In one example, the reset signal RS 186 is inactivated or goes to logic low based on a dead time of the circuit 100. In this description, a minimum separation required in time between two received photons so that they can be recorded distinctly by the circuit 100 is defined as the dead time of the circuit 100. The circuit 100 is ready to detect a new photon immediately after the CSA 120 is reset. Thus, the dead time of the circuit 100 is maintained constant by the active comparator 174 and the clock generator 180.

The high pass filter 140 filters any low frequency noise in the integrated signal VI 126, and thus prevents the low frequency noise from reaching the ADC 160 when no light is received by the photodiode 102 or when the system including circuit 100 is idle. The high pass filter 140 prevents any signal whose frequency is less than a cut-off frequency of the high pass filter 140 from reaching the ADC 160 and the active comparator 174. Thus, the circuit 100 provides a mechanism to activate the ADC 160 only when the light is received by the photodiode 102. If no light is received by the photodiode 102, the ADC 160 will not generate any count signal CNT 162. Also, the noise reduction circuit 150 filters the high frequency noise associated with the CSA 120. Accordingly, no additional power is required to reduce noise in the circuit 100. Therefore, the high pass filter 140 along with the noise reduction circuit 150 provides for dynamic shaping of noise.

When a photon is incident on the photodiode 102, the event signal EV 176 immediately goes to logic high which inactivates the high pass filter 140. This prevents ballistic deficit in the coarse signal VC 144. Also, this improves the signal gain which in turn improves the signal to noise ratio. Ballistic deficit is a droop in the coarse signal VC 144 that otherwise would have occurred if the high pass filter 140 had not been inactivated. The droop refers to a constant reduction in a signal level of the coarse signal VC 144.

Figure 2:
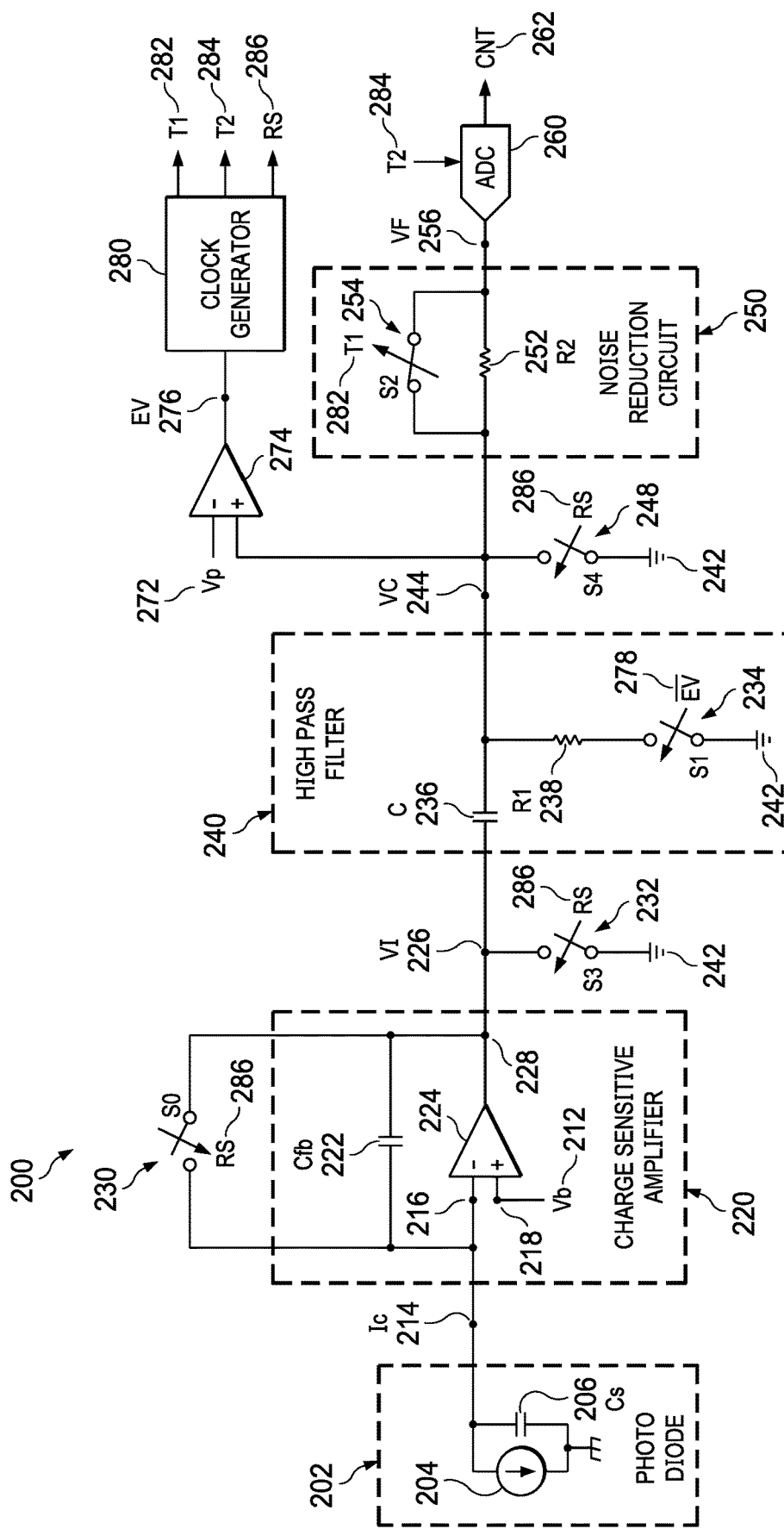
FIG. 2 is a schematic diagram of a circuit, according to an embodiment.

FIG. 2 is a schematic diagram of a circuit 200, according to an embodiment. The circuit 200 includes a photodiode 202 and a charge sensitive amplifier (CSA) 220. The photodiode 202, in one example, is modeled to include a sensor 204 and an associated capacitance Cs 206. The CSA 220 is coupled to the photodiode 202. The CSA 220 includes a primary transconductor 224 with an inverting terminal 216, a non-inverting terminal 218 and an output terminal 228. The photodiode 202 is coupled to the inverting terminal 216 of the primary transconductor 224. The non-inverting terminal 218 receives a bias voltage Vb 212. A feedback capacitor Cfb 222 is coupled between the inverting terminal 216 and the output terminal 228 of the primary transconductor 224. The circuit 200 also includes a reset switch S0 230 coupled in parallel to the feedback capacitor Cfb 222.

The circuit 200 includes a third switch S3 232 coupled to the CSA 220 and a ground terminal 242. The circuit 200 also includes a high pass filter 240 and a noise reduction circuit 250. The high pass filter 240 is coupled to the CSA 220. The high pass filter 240 includes a capacitor C 236, a primary resistor R1 238 and a first switch S1 234. The capacitor C 236 is coupled between the CSA 220 and the noise reduction circuit 250. The primary resistor R1 238 is coupled to the capacitor C 236. The first switch S1 234 is coupled to the primary resistor R1 238 and the ground terminal 242.

The circuit 200 includes a fourth switch S4 248 coupled between the high pass filter 240 and the ground terminal 242. The noise reduction circuit 250 is coupled to the high pass filter 240. The noise reduction circuit 250 includes a secondary resistor R2 252 and a second switch S2 254. The secondary resistor R2 252 is coupled to the high pass filter 240, and the second switch S2 254 is coupled in parallel to the secondary resistor R2 252. The circuit 200 includes an analog to digital converter (ADC) 260 coupled to the noise reduction circuit 250.

The circuit 200 also includes an active comparator 274 and a clock generator 280. The active comparator 274 is coupled to the high pass filter 240. The clock generator 280 is coupled to the active comparator 274. The circuit 200 may include one or more additional components that are not described herein for simplicity of the description.

In operation of the circuit 200 (FIG. 2), the photodiode 202 receives light which includes multiple photons of different energies. The photodiode 202 generates a proportional current signal Ic 214 when these photons are incident on the photodiode 202. In another example, the photodiode 202 receives an energy signal and generates the proportional current signal Ic 224. The sensor 204 receives the light, and the associated capacitance Cs 206 stores a charge proportional to the received light. The CSA 220 receives the current signal Ic 214 generated by the photodiode 202. The CSA 220 generates an integrated signal VI 226 in response to the current signal Ic 214. In one version, the CSA 220 integrates the current signal Ic 214 to generate the integrated signal VI 226. The CSA 220 receives the current signal Ic 214 at the inverting terminal 216 and the bias voltage Vb 212 at the non-inverting terminal 218. The integrated signal VI 226 is generated at the output terminal 228 of the primary transconductor 224. The reset switch S0 230 and the third switch S3 232 are closed by a reset signal RS 286. The reset switch S0 230 resets the CSA 220 when activated by the reset signal RS 286 by discharge of the feedback capacitor Cfb 222 through the third switch S3 232.

The high pass filter 240 receives the integrated signal VI 226 and an inverse of an event signal $\overline{EV}$ 278. The high pass filter 240 generates a coarse signal VC 244 in response to the integrated signal VI 226 and the inverse of the event signal $\overline{EV}$ 278. In one version, the high pass filter 240 filters the integrated signal VI 226 to generate the coarse signal VC 244. The first switch S1 234 is closed by an inverse of the event signal $\overline{EV}$ 278. The active comparator 274 receives the coarse signal VC 244 and a primary reference voltage signal Vp 272. The active comparator 274 compares the coarse signal VC 244 and the primary reference voltage signal Vp 272 and generates an event signal EV 276. The event gate EV 276 is provided to a NOT gate which generates the inverse of the event signal $\overline{EV}$ 278. Thus, the event signal EV 276 and the inverse of the event signal $\overline{EV}$ 278 are complement of each other.

The clock generator 280 generates a first trigger signal T1 282, a second trigger signal T2 284 and the reset signal RS 286 in response to the event signal EV 276 received from the active comparator 274. The clock generator 280 adds a first delay to the event signal EV 276 to generate the first trigger signal T1 282. The clock generator 280 adds a second delay to the event signal EV 276 to generate the second trigger signal T2 284. The clock generator 280 adds a third delay to the event signal EV 276 to generate the reset signal RS 286.

When the event signal EV 276 is at logic high, the clock generator 280 generates the first trigger signal T1 282 after the first delay, the second trigger signal T2 284 after the second delay and the reset signal RS 286 after the third delay. In one example, the third delay is greater than the second delay, and the second delay is greater than the first delay. In another example, the third delay is equal to the second delay.

The noise reduction circuit 250 receives the coarse signal VC 244 and the first trigger signal T1 282, and generates a fine signal VF 256. The second switch S2 254 is opened by the first trigger signal T1 282. The ADC 260 generates a count signal CNT 262 in response to the fine signal VF 256 and the second trigger signal T2 284. The third switch S3 232 and the fourth switch S4 248 are closed by the reset signal RS 286.

The first switch S1 234 in the high pass filter 240 is closed by the inverse of the event signal $\overline{EV}$ 278. Thus, the first switch S1 234 is closed when the event signal EV 276 is at logic low. This enables the high pass filter 240 to be operational while the event signal EV 276 is at logic low. Thus, the high pass filter 240 filters any low frequency noise in the integrated signal VI 226, and thus prevents the low frequency noise from reaching the ADC 260 when no light or a signal less than the primary reference voltage signal Vp 272 is received by the photodiode 202 or when the system including circuit 200 is idle. The high pass filter 240 prevents any signal whose frequency is less than a cut-off frequency of the high pass filter 240 from reaching the ADC 260 and the active comparator 274.

An 'event' occurs when an X-ray photon is incident on the photodiode 202, and a proportional current signal Ic 214 is generated. The CSA 220 generates the integrated signal VI 226 in response to the current signal Ic 214. The high pass filter 240 generates the coarse signal VC 244 in response to the integrated signal VI 226 and the inverse of the event signal $\overline{EV}$ 278. The active comparator 274 is always active. In one example, the active comparator 274 does not generate the event signal EV 276 when the coarse signal VC 244 is less than the primary reference voltage signal Vp 272. The active comparator 274 toggles or generates the event signal EV 276 when the coarse signal VC 244 is greater than the primary reference voltage signal Vp 272.

When the event signal EV 276 is generated, the first switch S1 234 is opened as the event signal EV 276 is at logic high. This disables the high pass filter 240. The clock generator 280 generates the first trigger signal T1 282, the second trigger signal T2 284 and the reset signal RS 286 in response to the event signal EV 276 received from the active comparator 274. The first trigger signal T1 282, the second trigger signal T2 284 and the reset signal RS 286 are generated only when the event signal EV 276 is at logic high.

The clock generator 280 adds a first delay to the event signal EV 276 to generate the first trigger signal T1 282. In one example, the first delay is equivalent to a time consumed by the circuit 200 to acquire most of the charge when the light that includes multiple photons is received by the photodiode 202. The exact value of the first delay is optimized for minimum noise in the fine signal VF 256 at the end of the second delay based on a transient response of the photodiode 202 and the CSA 220. In another example, the first delay is equal to a predefined time after the event signal EV 276 is generated. In yet another example, the first delay is in a range of 4-20 nano seconds after the event signal EV 276 is generated.

The second switch S2 254 in the noise reduction circuit 250 is normally in closed state. On receiving the first trigger signal T1 282 from the clock generator 280, the second switch S2 254 is opened. This results in blocking of any high frequency noise of the CSA 220 sampled by the capacitor C 236. A high resistance of the secondary resistor R2 252 in combination with a capacitor in the ADC 260 functions as a low pass filter and filters any high frequency noise from the CSA 220 or the high pass filter 240. The second switch S2 254 is closed when the first trigger signal T1 282 is inactivated. In one version, the second switch S2 254, remains open for a predefined interval. In another version, the second switch S2 254 is closed before generation of the second trigger signal T2 284, so the first trigger signal T1 282 is inactivated before generation of the second trigger signal T2 284. Thus, any high frequency noise of the CSA 220 is removed by the noise reduction circuit 250. As a result, no additional power is required to reduce noise in the circuit 200.

The clock generator 280 adds the second delay to the event signal EV 276 to generate the second trigger signal T2 284. On receiving the second trigger signal T2 284, the ADC 260 samples the fine signal VF 256 to generate the count signal CNT 262. A time interval during which the second trigger signal T2 284 is activated or is at logic high depends on a sampling frequency of the ADC 260.

The clock generator 280 adds a third delay to the event signal EV 276 to generate the reset signal RS 286. In one example, the reset signal RS 286 is generated by the clock generator 280 when the second trigger signal T2 284 is inactivated. The reset signal RS 286 closes the reset switch S0 230, the third switch S3 232 and the fourth switch S4 248. The closing of the reset switch S0 230 causes resetting of the CSA 220.

The closing of the third switch S3 232 and the fourth switch S4 248 causes discharge of the capacitor C 236, and also causes the event signal EV 276 to go to logic low. This enables the high pass filter 240 to filter any low frequency noise in the integrated signal VI 226, and thus prevents the low frequency noise from reaching the ADC 260 when no light or a signal less than the primary reference voltage signal Vp 272 is received by the photodiode 202 or when the system including circuit 200 is idle. The high pass filter 240 prevents any signal whose frequency is less than a cut-off frequency of the high pass filter 240 from reaching the ADC 260 and the active comparator 274. In one example, the reset signal RS 286 is inactivated or goes to logic low based on a dead time of the circuit 200. In this description, a minimum separation required in time between two received photons so that they can be recorded distinctly by the circuit 200 is defined as the dead time of the circuit 200. The circuit 200 is ready to detect a new photon immediately after the CSA 220 is reset. Thus, the dead time of the circuit 200 is maintained constant by the active comparator 274 and the clock generator 280.

The high pass filter 240 filters any low frequency noise in the integrated signal VI 226, and thus prevents the low frequency noise from reaching the ADC 260 when no light or a signal less than the primary reference voltage signal Vp 272 is received by the photodiode 202 or when the system including circuit 200 is idle. Thus, the circuit 200 provides a mechanism to activate the ADC 260 only when the light is received by the photodiode 202. If no light is received by the photodiode 202, the ADC 260 will not generate any count signal CNT 262. Also, the noise reduction circuit 250 filters the high frequency noise associated with the CSA 220. Accordingly, no additional power is required to reduce noise in the circuit 200. Therefore, the high pass filter 240 along with the noise reduction circuit 250 provides for dynamic shaping of noise.

When a photon is incident on the photodiode 202, the event signal EV 276 immediately causes switch S1 234 to disconnect from the ground terminal 242. This prevents ballistic deficit in the coarse signal VC 244. Also, this improves the signal gain which in turn improves the signal to noise ratio. Ballistic deficit is a droop in the coarse signal VC 244 that otherwise would have occurred if the high pass filter 240 had not been inactivated. The droop refers to a constant reduction in a signal level of the coarse signal VC 244 which discharges to the ground terminal 242 through the discharge path that includes the primary resistor R1 238 and the first switch S1 234.

Figure 3:
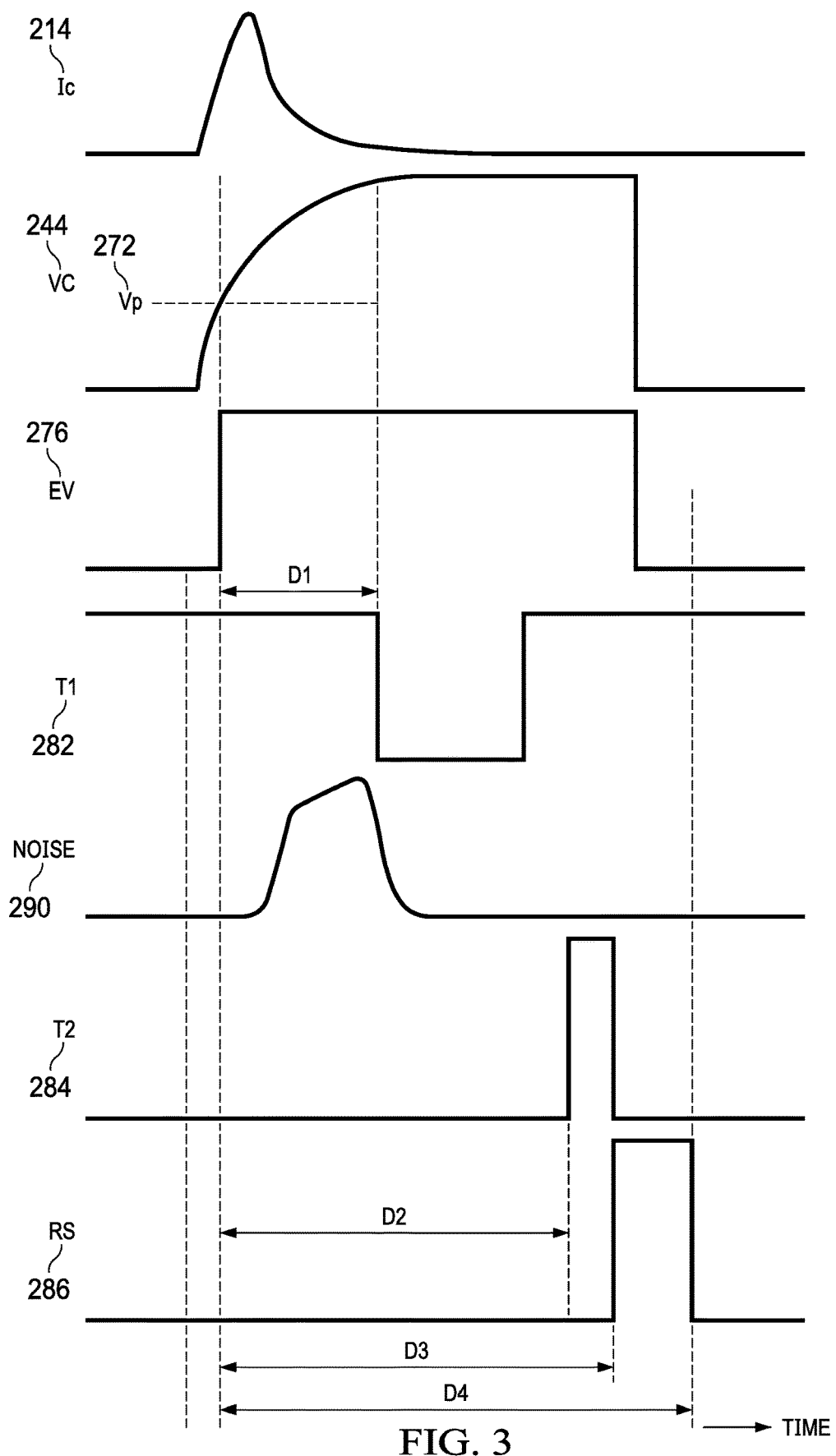
FIG. 3 is a timing diagram of operation of the circuit of FIG. 2, according to an embodiment.

FIG. 3 is a timing diagram of operation of the circuit 200. The FIG. 3 illustrates the current signal Ic 214, the coarse signal VC 244, the event signal EV 276, the first trigger signal T1 282, a noise 290, the second trigger signal T2 284 and the reset signal RS 286.

An 'event' occurs when an X-ray photon is incident on the photodiode 202 and a proportional current signal Ic 214 is generated. The current signal Ic 224 is illustrated in the timing diagram. The CSA 220 generates the integrated signal VI 226 in response to the current signal Ic 224. The high pass filter 240 generates the coarse signal VC 244 in response to the integrated signal VI 226 and an inverse of the event signal EV 276. The active comparator 274 is always active. The active comparator 274 does not generate the event signal EV 276 when the coarse signal VC 244 is less than the primary reference voltage signal Vp 272. As illustrated in the timing diagram, the event signal EV 276 is generated by the active comparator 274 when the coarse signal VC 244 is greater than the primary reference voltage signal Vp 272.

When the event signal EV 276 is generated, the first switch S1 234 is opened because the event signal EV 276 is at logic high. This disables high pass filter 240. The clock generator 280 generates a first trigger signal T1 282, a second trigger signal T2 284 and the reset signal RS 286 in response to the event signal EV 276 received from the active comparator 274. The clock generator 280 adds a first delay D1 to the event signal EV 276 to generate the first trigger signal T1 282. The clock generator 280 adds a second delay D2 to the event signal EV 276 to generate the second trigger signal T2 284. The clock generator 280 adds a third delay D3 to the event signal EV 276 to generate the reset signal RS 286.

When the event signal EV 276 is high, the clock generator 280 generates the first trigger signal T1 282 after the first delay D1, the second trigger signal T2 284 after the second delay D2 and the reset signal RS 286 after the third delay D3. In one example, the third delay D3 is greater than the second delay D2, and the second delay D2 is greater than the first delay D1. In another example, the third delay D3 is equal to the second delay D2. The first trigger signal T1 282, the second trigger signal T2 284 and the reset signal RS 286 are pulsed signals.

As illustrated in the timing diagram, the noise 290 represents a total integrated noise associated with the CSA 220. The noise 290 builds up after the event signal EV 276 goes to logic high. The noise 290 represents charge accumulated across the capacitor C 236. The noise 290 represents noise across entire frequency spectrum. The high pass filter 240 filters any low frequency noise in the integrated signal VI 226, and thus prevents the low frequency noise from reaching the ADC 260 when no light or a signal less than the primary reference voltage signal Vp 272 is received by the photodiode 202 or when the system including circuit 200 is idle. The high pass filter 240 prevents any signal whose frequency is less than a cut-off frequency of the high pass filter 240 from reaching the ADC 260 and the active comparator 274. The second switch S2 254 in the noise reduction circuit 250 is always in closed state. On receiving the first trigger signal T1 282 from the clock generator 280, the second switch S2 254 is opened. This reduces the noise 290.

The second switch S2 254 is closed before generation of the second trigger signal T2 284 i.e. the first trigger signal T1 282 is inactivated before generation of the second trigger signal T2 284. On receiving the second trigger signal T2 284, the ADC 260 samples the fine signal VF 256 to generate the count signal CNT 262. A time interval, during which the second trigger signal T2 284 is activated or is at logic high depends on a sampling frequency of the ADC 260.

The reset signal RS 286 is generated by the clock generator 280 when the second trigger signal T2 284 is inactivated. The reset signal RS 286 closes the reset switch S0 250, the third switch S3 232 and the fourth switch S4 248. The closing of the reset switch S0 250 causes resetting of the CSA 220.

The closing of the third switch S3 232 and the fourth switch S4 248 causes discharge of the capacitor C 236, and also the event signal EV 276 goes to logic low. This enables the high pass filter 240 to filter any low frequency noise in the integrated signal VI 226, and thus prevents the low frequency noise from reaching the ADC 260 when no light or a signal less than the primary reference voltage signal Vp 272 is received by the photodiode 202 or when the system including circuit 200 is idle. In one example, the reset signal RS 286 is inactivated or goes to logic low based on a dead time D4 of the circuit 200. In this description, a minimum separation required in time between two received photons so that they can be recorded distinctly by the circuit 200 is defined a dead time of the circuit 200 and represented as D4. The circuit 200 is ready to detect a new photon immediately after the CSA 220 is reset. Thus, the dead time D4 of the circuit 200 is maintained constant by the active comparator 274 and the clock generator 280. In another implementation, the third switch S3 232 and the fourth switch S4 248 are not present or are not closed on receiving the reset signal RS 286. In such a case, the dead time D4 is determined by energy of photons incident on the photodiode 202 and a time constant of the high pass filter 240.

The high pass filter 240 filters any low frequency noise in the integrated signal VI 226, and thus prevents the low frequency noise from reaching the ADC 260 when no light or a signal less than the primary reference voltage signal Vp 272 is received by the photodiode 202 or when the system including circuit 200 is idle. Thus, the circuit 200 provides a mechanism to activate the ADC 260 only when the light is received by the photodiode 202 or when an event is detected. If no light is received by the photodiode 202, the ADC 260 will not generate any count signal CNT 262. Also, the noise reduction circuit 250 filters the high frequency noise associated with the CSA 220. Accordingly, no additional power is required to reduce noise in the circuit 200. Therefore, the high pass filter 240 along with the noise reduction circuit 250 provides for dynamic shaping of noise.

When a photon is incident on the photodiode 202, the event signal EV 276 immediately causes switch S1 234 to disconnect from the ground terminal 242. This prevents ballistic deficit in the coarse signal VC 244. Also, this improves the signal gain which in turn improves the signal to noise ratio. Ballistic deficit is a droop in the coarse signal. The droop refers to a constant reduction in a signal level of the coarse signal VC 244 which discharges to the ground terminal 242 through the discharge path that includes the primary resistor R1 238 and the first switch S1 234.

Figure 4:
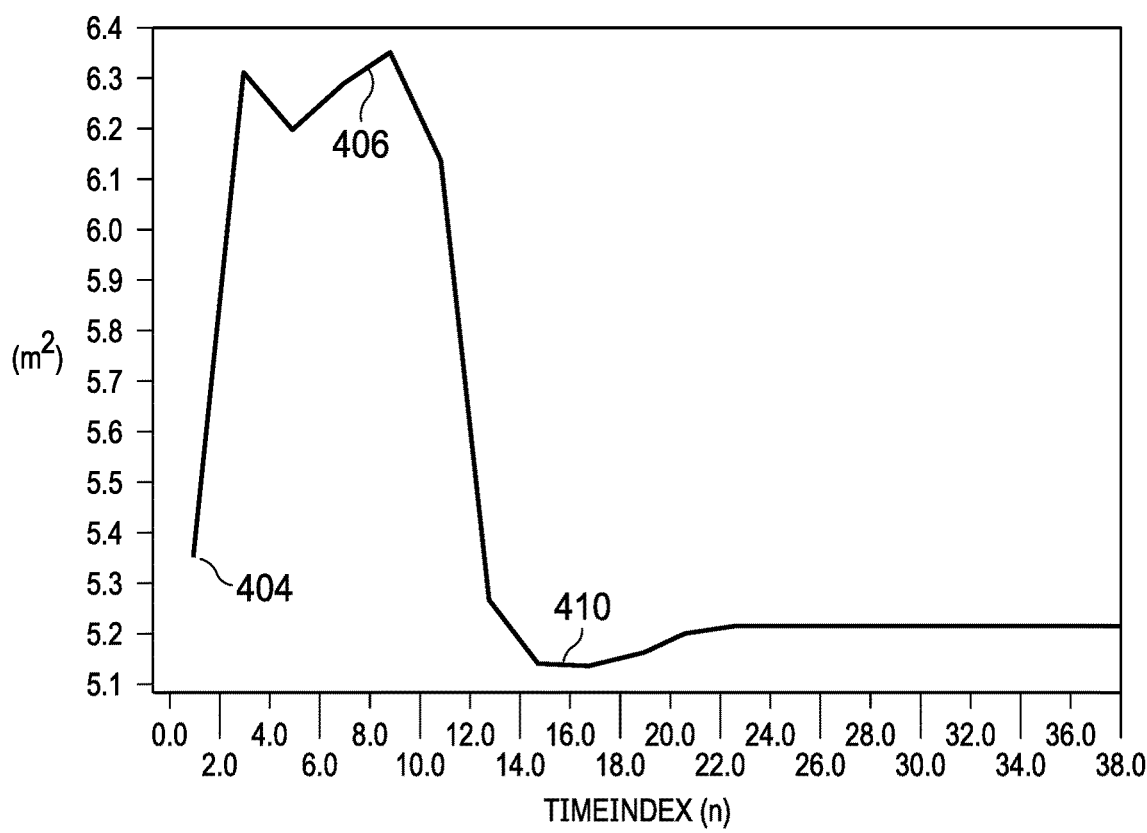
FIG. 4 is a graph of noise in the circuit of FIG. 2, as it varies with time, according to an embodiment.

FIG. 4 is a graph of noise in the circuit of FIG. 2, as it varies with time, according to an embodiment. At 404, the circuit 200 detects an event in which an X-ray photon is incident on the photodiode 202. As a result, the event signal EV 276 is at logic high. This disables the high pass filter 240. The disabling of the high pass filter 240 prevent ballistic deficit of the coarse signal VC 244 but causes noise to increase with time.

At 406, the first trigger signal T1 282 is received by the noise reduction circuit 250. The second switch S2 in the noise reduction circuit 250 is always in closed state. On receiving the first trigger signal T1 282 from the clock generator 280, the second switch S2 254 is opened, which blocks the high frequency noise associated with the CSA 220. A high resistance of the secondary resistor R2 252 in combination with a capacitor in the ADC 260 function as a low pass filter and filters any high frequency noise from the CSA 220 or the high pass filter 240. The first trigger signal T1 282 is inactivated before generation of the second trigger signal T2 284.

At 410, the second trigger signal T2 284 is received by the ADC 260 which samples the fine signal VF 256 to generate the count signal CNT 262. Thus, the circuit 200 ensures that the ADC 260 samples the fine signal VF 256 only when the noise in the circuit 200 is low. This also helps the circuit 200 to achieve better energy resolution.

Figure 5:
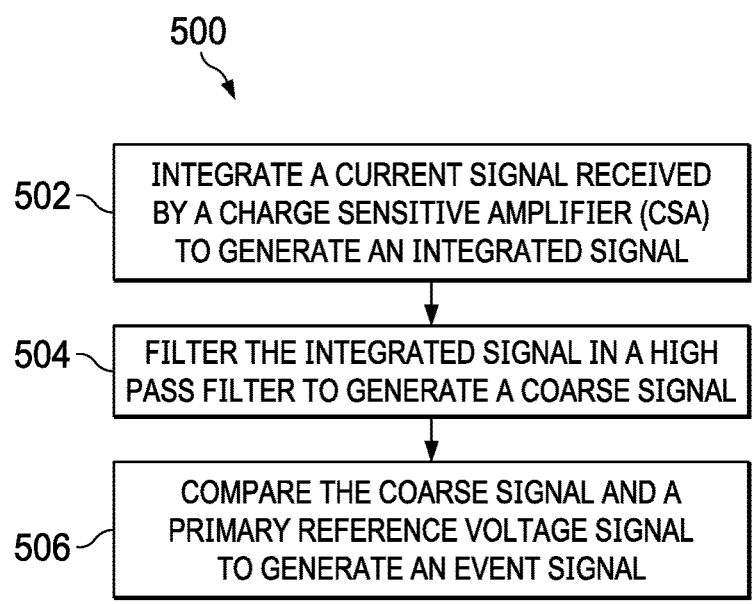
FIG. 5 is a flowchart of a method of operation of a circuit, according to an embodiment.

FIG. 5 is a flowchart 500 of a method of operation of a circuit, according to an embodiment. The flowchart 500 is explained in connection with the circuit 200. At step 502, a current signal received by a charge sensitive amplifier (CSA) is integrated to generate an integrated signal. For example, in circuit 200, an 'event' occurs when light that includes multiple photons is received by the photodiode 202 and a proportional current signal Ic 214 is generated. The CSA 220 integrates the current signal Ic 214 to generate the integrated signal VI 226. The CSA 220 includes a primary transconductor 224 with an inverting terminal 216, a non-inverting terminal 218 and an output terminal 228. The CSA 220 receives the current signal Ic 214 at the inverting terminal 216 and the bias voltage Vb 212 at the non-inverting terminal 218. The integrated signal VI 226 is generated at the output terminal 228 of the primary transconductor 224.

At step 504, the integrated signal is filtered in a high pass filter to generate a coarse signal. In circuit 200, the high pass filter 240 filters the integrated signal VI 226 to generate the coarse signal VC 244. The first switch S1 234 in the high pass filter 240 is closed by an inverse of the event signal $\overline{EV}$ 278.

At step 506, the coarse signal and a primary reference voltage signal are compared to generate an event signal. In circuit 200, the active comparator 274 compares the coarse signal VC 244 and the primary reference voltage signal Vp 272 and generates the event signal EV 276. The active comparator 274 is always active. The active comparator 274 does not generate the event signal EV 276 when the coarse signal VC 244 is less than the primary reference voltage signal Vp 272. The active comparator 274 toggles or generates the event signal EV 276 when the coarse signal VC 244 is greater than the primary reference voltage signal Vp 272. When the event signal EV 276 is generated, the first switch S1 234 is opened as the event signal EV 276 is at logic high. This disables or inactivates the high pass filter 240.

According to the method, when the event signal is at logic high, adding a first delay to the event signal to generate the first trigger signal and adding a second delay to the event signal to generate the second trigger signal. A third delay is added to the event signal to generate the reset signal.

A noise reduction circuit is coupled to the high pass filter. A second switch in the noise reduction circuit is always in closed state. On receiving the first trigger signal, the second switch is opened, which blocks a high frequency noise associated with the CSA 220. A high resistance of a secondary resistor in the noise reduction circuit and a capacitor in the ADC function as a low pass filter and filters any high frequency noise from the CSA 220 or the high pass filter 240. The noise reduction circuit receives the coarse signal and the first trigger signal, and generates a fine signal VF 256. The second switch is opened by the first trigger signal. The ADC generates a count signal in response to the fine signal and the second trigger signal. On receiving the second trigger signal, the ADC samples the fine signal to generate the count signal.

According to the method, a high pass filter filters any low frequency noise in the integrated signal, and thus prevents the low frequency noise from reaching the ADC when no light or a signal less than the primary reference voltage signal is received by the photodiode or when the system including circuit 200 is idle. Thus, the method activates the ADC only when the light is received by the photodiode. If no light is received by the photodiode, the ADC will not generate any count signal.

When a photon is incident on the photodiode 202, the event signal EV 276 immediately causes switch S1 234 to disconnect from the ground terminal 242. This prevents ballistic deficit in the coarse signal VC 244. Also, this improves the signal gain which in turn improves the signal to noise ratio. Ballistic deficit is a droop in the coarse signal VC 244 that otherwise would have occurred if the high pass filter 240 had not been inactivated. Also, the noise reduction circuit filters the high frequency noise associated with the CSA. Accordingly, no additional power is required to reduce noise in the circuit 200. Therefore, the high pass filter 240 along with the noise reduction circuit 250 provides for dynamic shaping of noise.

Figure 6:
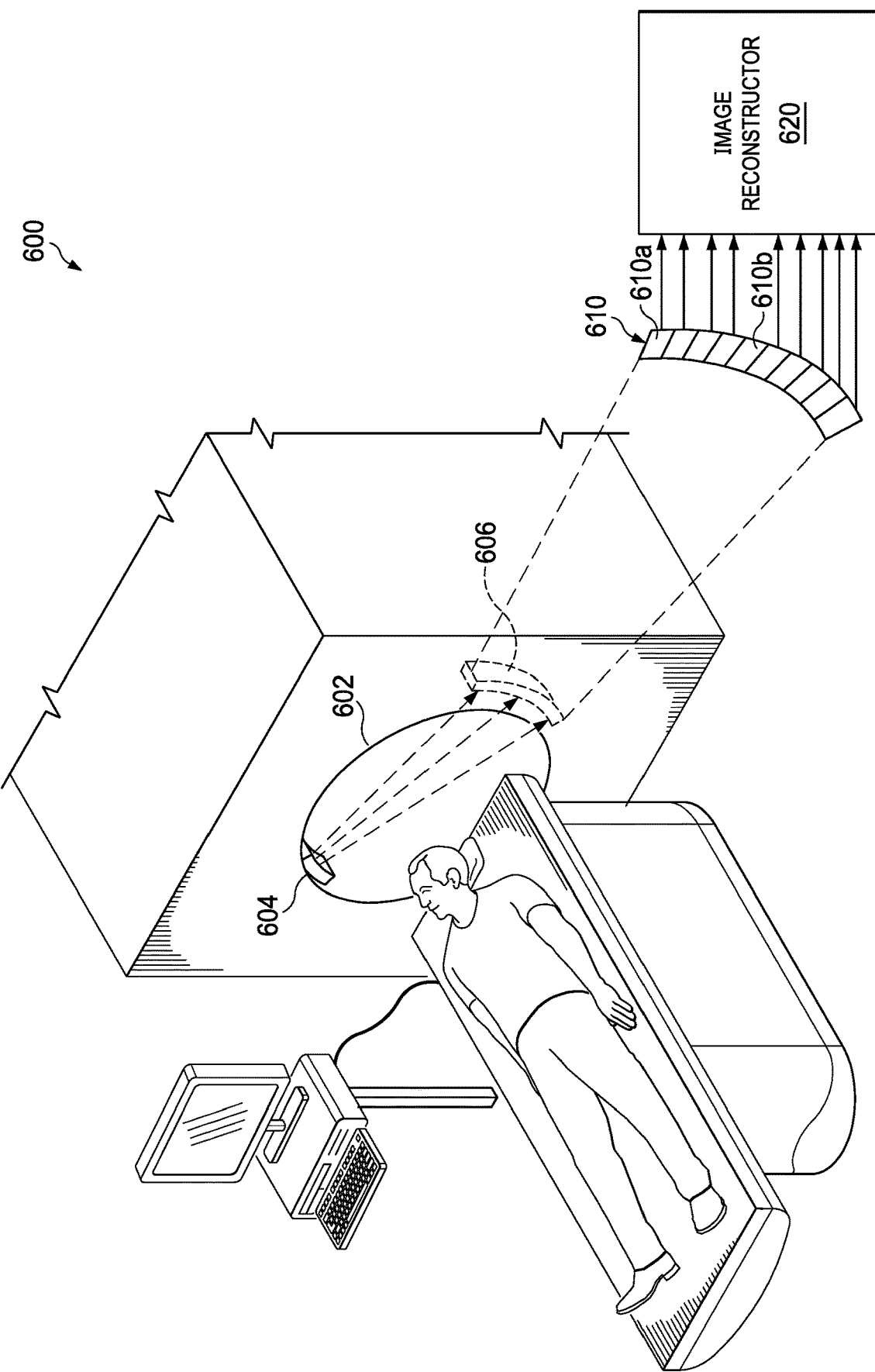
FIG. 6 illustrate an imaging system, according to an embodiment.

FIG. 6 illustrates an imaging system 600, according to an embodiment. In one version, the imaging system 600 is a CT (computed tomography) imaging system. The imaging system 600 includes a gantry 602 that receives a patient. The gantry 602 rotates at a defined speed. In one example, a controller provides the defined speed to the gantry 602.

An x-ray source 604 is disposed in the gantry 602. The x-ray source 604 emits x-rays towards the patient. The x-rays are attenuated by the patient and received by a receiver 606. Many scans are taken progressively as the patient/object is gradually passed through the gantry. In FIG. 6, a cross-section of the receiver 606 is enlarged and illustrated for better clarity. The cross-section includes multiple detectors 610.

The multiple detectors 610 receive x-rays attenuated by the patient. The multiple detectors 610 include detectors 610a and 610b. At least one detector of the multiple detectors 610 generates a current signal in response to the received attenuated x-rays. At least one detector is similar to the circuit 200 (illustrated in FIG. 2) in connection and operation. In one example, the detector 610b is similar to the circuit 200 in connection and operation. The photodiode in the detector 610b generates the current signal in response to the received attenuated x-rays from the patient.

The detector 610b similar to the circuit 200 includes a charge sensitive amplifier (CSA), a high pass filter, an active comparator, a clock generator, a noise reduction circuit and an analog to digital converter (ADC). The high pass filter prevents any low frequency noise from reaching the ADC when no attenuated x-rays is received by the photodiode or when the imaging system 600 is idle. Thus, the detector 610b provides a mechanism to activate the ADC only when the attenuated x-rays is received by the photodiode or when an event is detected. If no attenuated x-rays is received by the photodiode, the ADC will not generate any count signal. Also, the noise reduction circuit filters a high frequency noise associated with the CSA. Accordingly, no additional power is required to reduce noise in the detector 610b.

The image reconstructor 620 receives the digital signal from each detector of the multiple detectors 610 to create an image of a part of patient which is being scanned by the imaging system 600. The image reconstructor 620, in one example, includes a processor. The processor can be, for example, a CISC-type (Complex Instruction Set Computer) CPU, RISC-type CPU (Reduced Instruction Set Computer), or a digital signal processor (DSP). The image reconstructor 620, in one example, is disposed outside the imaging system 600. The imaging system 600 may include one or more additional components that are not described herein for simplicity of the description.

Modifications are possible in the described embodiments, and other embodiments are possible, within the scope of the claims.

What is claimed is:

1. A circuit comprising:
    a charge sensitive amplifier (CSA) configured to generate an integrated signal in response to an input signal;
    a filter coupled to the CSA and configured to receive the integrated signal and an event signal, the filter configured to generate a filtered output signal; and
    a comparator coupled to the filter and configured to receive a primary reference voltage signal and generate the event signal.

2. The circuit of claim 1 further comprising a clock generator coupled to the comparator and configured to generate a first trigger signal, a reset signal and a second trigger signal in response to the event signal.

3. The circuit of claim 2 further comprising a noise reduction circuit coupled to the filter and configured to:
    receive the filtered output signal and the first trigger signal; and
    generate a fine signal.

4. The circuit of claim 3 further comprising an analog to digital converter (ADC) coupled to the noise reduction circuit and configured to generate a count signal in response to the fine signal and the second trigger signal.

5. The circuit of claim 4, wherein the CSA comprises:
    a primary transconductor having:
        an inverting terminal configured to receive the input signal;

a non-inverting terminal configured to receive a bias voltage; and
an output terminal configured to generate the integrated signal; and
a feedback capacitor coupled between the inverting terminal and the output terminal of the primary transconductor.

6. The circuit of claim 5 further comprising a reset switch coupled in parallel to the feedback capacitor and configured to reset the CSA when closed by the reset signal.

7. The circuit of claim 3, wherein the filter comprises:
a capacitor coupled between the CSA and the noise reduction circuit;
a primary resistor coupled to the capacitor; and
a first switch coupled to the primary resistor and a ground terminal, and configured to be closed by an inverse of the event signal.

8. The circuit of claim 3, wherein the noise reduction circuit further comprises:
a secondary resistor coupled to the filter and configured to receive the filtered output signal; and
a second switch coupled in parallel to the secondary resistor and configured to be opened by the first trigger signal.

9. The circuit of claim 2, wherein the clock generator is configured to:
generate the first trigger signal after a first delay following the event signal;
generate the second trigger signal after a second delay following the event signal; and
generate the reset signal after a third delay following the event signal.

10. The circuit of claim 7 further comprising:
a third switch coupled to the CSA and the ground terminal, and configured to be closed by the reset signal; and
a fourth switch coupled between the filter and the ground terminal, and configured to be closed by the reset signal.

11. The circuit of claim 1, wherein:
the input signal is a current signal;
the filter is a high pass filter;
the filtered output signal is a coarse signal; and
the comparator is an active comparator.

12. A method comprising:
integrating an input signal received by a charge sensitive amplifier (CSA) to generate an integrated signal;
filtering the integrated signal in a filter to generate a filtered output signal, the filter configured to receive an event signal; and
comparing the filtered output signal and a primary reference voltage signal to generate the event signal.

13. The method of claim 12 further comprising:
generating a first trigger signal after a first delay following the event signal;
generating a second trigger signal after a second delay following the event signal; and
generating a reset signal after a third delay following the event signal.

14. The method of claim 13, wherein the first trigger signal, the second trigger signal and the reset signal are generated following a transition of the event signal to a logic high.

15. The method of claim 13 further comprising inactivating the filter through a first switch when the event signal is high.

16. The method of claim 13 further comprising generating a fine signal by a noise reduction circuit in response to the filtered output signal and the first trigger signal.

17. The method of claim 16 further comprising opening a second switch in the noise reduction circuit by the first trigger signal, the second switch coupled between the filter and an analog to digital converter (ADC).

18. The method of claim 17 further comprising generating a count signal by the ADC in response to the fine signal and the second trigger signal.

19. An imaging system comprising:
a gantry configured to receive a patient and rotate at a defined speed;
an x-ray source disposed in the gantry and configured to emit x-rays towards the patient; and
a plurality of detectors configured to receive to receive x-rays attenuated by the patient, at least one detector of the plurality of detectors configured to generate an input signal in response to the received attenuated x-rays, the at least one detector comprising:
a charge sensitive amplifier (CSA) configured to generate an integrated signal in response to the input signal;
a filter coupled to the CSA and configured to receive the integrated signal and an event signal, the filter configured to generate a filtered output signal; and
a comparator coupled to the filter and configured to receive the filtered output signal and a primary reference voltage signal and generate the event signal.

20. The imaging system of claim 19 further comprising a noise reduction circuit coupled to the filter and configured to: receive the filtered output signal and a first trigger signal; and generate a fine signal.

21. The imaging system of claim 20, wherein the filter comprises:
a capacitor coupled between the CSA and the noise reduction circuit;
a primary resistor coupled to the capacitor; and
a first switch coupled to the primary resistor and a ground terminal, and configured to be closed by an inverse of the event signal.

* * * * *